US010054429B2

(12) United States Patent
Arieli et al.

(10) Patent No.: US 10,054,429 B2
(45) Date of Patent: Aug. 21, 2018

(54) SYSTEM FOR TOMOGRAPHY AND/OR TOPOGRAPHY MEASUREMENTS OF A LAYERED OBJECTS

(71) Applicant: ADOM, Advanced Optical Technologies Ltd., Lod (IL)

(72) Inventors: Yoel Arieli, Jerusalem (IL); Yoel Cohen, Nes Ziona (IL)

(73) Assignee: ADOM, ADVANCED OPTICAL TECHNOLOGIES LTD., Lod (IL)

( * ) Notice: Subject to any disclaimer, the term of this patent is extended or adjusted under 35 U.S.C. 154(b) by 0 days.

(21) Appl. No.: 15/311,280

(22) PCT Filed: May 14, 2015

(86) PCT No.: PCT/IL2015/050511
§ 371 (c)(1),
(2) Date: Nov. 15, 2016

(87) PCT Pub. No.: WO2015/177784
PCT Pub. Date: Nov. 26, 2015

(65) Prior Publication Data
US 2017/0074644 A1    Mar. 16, 2017

Related U.S. Application Data

(60) Provisional application No. 61/994,902, filed on May 18, 2014.

(51) Int. Cl.
*G01B 11/25* (2006.01)
*G01N 21/47* (2006.01)
(Continued)

(52) U.S. Cl.
CPC ......... *G01B 11/25* (2013.01); *G01N 21/4795* (2013.01); *H04N 5/2254* (2013.01);
(Continued)

(58) Field of Classification Search
CPC .. G01B 11/25; G01B 2210/50; H04N 5/2256; H04N 5/2254; G01N 21/4795; G01N 21/39; G01N 2021/1787
See application file for complete search history.

(56) References Cited

U.S. PATENT DOCUMENTS 7,751,063 B2 * 7/2010 Dillon ................ G01B 11/2527
356/497
2010/0099984 A1 * 4/2010 Graser ................... G01B 11/24
600/425

(Continued)

FOREIGN PATENT DOCUMENTS

DE    10 2011 117523    4/2013
FR    2758076    7/1998

OTHER PUBLICATIONS

Ruprecht A K et al: "Chromatic Confocal Detection for High-Speed Microtopography Measurements", Proceedings of SPIE, S P I E—International Society for Optical Engineering, US, vol. 5302, No. 1, Jan. 1, 2003 (Jan. 1, 2003), pp. 53-60.
Tiziani H J et al: "Three-Dimensional Image Sensing by Chromatic Confocal Microscopy", Applied Optics, Optical Society of America, Washington, DC; US, vol. 33, No. 10, Apr. 1, 1994 (Apr. 1, 1994), pp. 1838-1843.
(Continued)

*Primary Examiner* — Gevell Selby
(74) *Attorney, Agent, or Firm* — Workman Nydegger

(57) ABSTRACT

A system (10) for analyzing an object (11) includes a light source (12) producing multiple light components, each of different wavelength and a respective amplitude, phase and polarization. An optical element (13) directs the light components on to the object to create known 2D patterns at different image planes displaced from the optical element by distances that are known functions of the wavelength of the light component. A 2D imager (20) images the 2D patterns and produces a plurality of full view 2D wavelength dependent patterns each corresponding to a known distance from the optical element and each having variable image contrast dependent on displacement of a surface of the object from (Continued)

the image plane, maximal image contrast being achieved when the surface of the object and image plane are coincident. A processing unit (25) determines the object surface based on the variable image contrast of each image.

19 Claims, 2 Drawing Sheets

(51) Int. Cl.
*H04N 5/225* (2006.01)
*G01N 21/39* (2006.01)
*G01N 21/17* (2006.01)

(52) U.S. Cl.
CPC ....... *H04N 5/2256* (2013.01); *G01B 2210/50* (2013.01); *G01N 21/39* (2013.01); *G01N 2021/1787* (2013.01)

(56) References Cited

U.S. PATENT DOCUMENTS

| | | | |
|---|---|---|---|
| 2011/0279670 A1 | 11/2011 | Park et al. | |
| 2012/0267515 A1* | 10/2012 | Wu | G02B 21/0044 250/214 P |
| 2012/0310083 A1* | 12/2012 | Friedman | A61B 3/10 600/431 |
| 2014/0285812 A1* | 9/2014 | Levitz | A61B 5/0066 356/479 |
| 2015/0168125 A1* | 6/2015 | Arieli | A61B 3/102 351/211 |

OTHER PUBLICATIONS

International Search Report and Written Opinion for application No. PCT/IL2015/050511 dated Nov. 20, 2015.

* cited by examiner

SYSTEM FOR TOMOGRAPHY AND/OR TOPOGRAPHY MEASUREMENTS OF A LAYERED OBJECTS

FIELD OF THE INVENTION

This invention relates to tomography and/or topography measurements by use of a 2D imaging system with chromatic aberration.

BACKGROUND OF THE INVENTION

In many technical fields there is a need for measuring and imaging the tomography and/or the topography of transparent or semi-transparent objects. There are many optical methods for accomplishing at least part of this task, such as the structured-light scanning method, confocal microscopy, phase shift method, optical coherence tomography or holography. In some methods, the chromatic aberration of the optical system can prevent accurate measurement while some methods may advantageously exploit the chromatic aberration. For example, in the structured-light scanning methods, dispersion or chromatic aberration can lead to blurring of the structured-light pattern, which reduces the resolution. Alternatively, in chromatic confocal microscopy, a suitable objective lens having multiple focal lengths that are dependent on wavelength is used to image a point or an array of point sources of wideband-spectrum light. As a result, depending on the wavelengths of the components of the illumination source emanating from the point sources, the illuminated point sources are imaged to different image planes having a range determined by the minimum and maximum wavelengths of the wideband illumination source.

An object located within this range reflects the light at each image plane, the reflected light being re-imaged into the pinhole or pinhole array by the objective lens. The intensity of the reflected light depends on the extent to which the image plane and the points of the object's surface that reflect the light coincide. Specifically, if an image plane coincides with points of the object, which may lie on one or more surfaces of the object, then the intensity of the light reflected by these points of the object will be maximal. The maximum intensity is detected for the particular wavelength that is imaged in focus at a particular point on the object's surface or one of its layer's surfaces. Thus, by determining the spectral peak position, the distance of the object's surface or of its layer's surfaces to the objective lens at this point and hence the object's tomography and/or topography may be determined. The evaluation is performed point-by-point using a spectrometer or line-by-line using a line spectrometer with camera chip. In particular, the multi-focus arrangement, preferably in combination with a micro-lens array and a matched pinhole array, is a promising option on account of the low expected time requirements for image recording.

U.S. Pat. No. 8,515,528 describes such a measuring arrangement and method for the three-dimensional measurement of at least part of an object includes a light source with a continuous spectrum, a device for generating a multifocal lighting pattern, a lens with a large chromatic aberration for imaging foci of the lighting pattern on the object, a detection unit for generating the wavelength spectrum of the foci that are confocally imaged on the object via the lens, and a spectrum-dispersive device disposed between the confocally imaged foci and the detection device.

EP-B-0 321 529 discloses a measuring arrangement for measuring the distances between an objective lens with high chromatic aberration and an object. A black-and-white CCD camera is used as detector, in front of which is arranged a spectrum-dispersing apparatus with an input slit. The wavelength information for each point is converted to location information to obtain a profile image of the surface of the object.

EP-B-0 466 979 discloses an arrangement for confocal and simultaneous picture generation with a moving pinhole diaphragm in the illumination ray path with a position-measuring system, a raster camera and a processing device for the raster camera, which synchronously reads out the pixels of the pinhole diaphragm.

US 2004/109170 discloses a sensor for rapid optical distance measurement based on the confocal imaging principle. The sensor includes a light source, which emits an illuminating light with different spectral components, and an optical imaging system, through which the illuminating light is directed onto the surface of a measurement object. Different spectral components of the illuminating light are focused at different distances from the optical imaging system due to a chromatic aberration of the optical imaging system. Also provided is a beam splitter, arranged so that measuring light reflected back at least partially from the surface, is separated spatially from the beam path of the illuminating light. Further, a light receiver is included, which records the measuring light, separated spatially from the beam path of the illuminating light, with spectral resolution. Finally, an analysis unit determines the distance between the sensor and the surface from the intensities of measuring light recorded for different spectral components. Such a system requires a pinhole for point by point imaging and a scanner that scans each image point to construct a 2D image.

DE-A-103 21 885 is also a confocal measuring arrangement for the three-dimensional measuring of an object with chromatic depth resolution, in which a multitude of foci are generated by means of a micro-lens array and are imaged onto the object. The reflected light is focused back into the plane of the micro lens foci. This arrangement is used to measure two or three-dimensional micro-profiles of a test objects of two or three-dimensional profiles of reflectivity or transparency.

It is thus known in the art to determine the distance between the sensor and the surface from the intensities of measuring light recorded for different spectral components.

SUMMARY OF THE INVENTION

It is an object of the invention to provide an alternative approach that facilitates full field tomography by producing a 2D image directly without the need for a scanner and where the distance between the sensor and the surface is determined not from the intensity but from the image contrast of measuring light recorded for different spectral components.

This object is realized in accordance with the invention by a system for analyzing an object having the features of claim 1.

In one embodiment the system comprises a broadband light source, an optical element such as a transparency, a micro lens array or a diffractive optical element in a transmissive or reflective mode that creates a known pattern that may or may not be different for different wavelengths, an objective lens with high chromatic aberration for imaging the pattern on to the object, and a spectral imager to determine the wavelength dependent image of the object. When a certain wavelength is focused on at least part of the object's surface or part of one of its layer's surfaces, a high contrast of the pattern at that wavelength is obtained on that part of the surface. In all other parts of surfaces that are not in focus, the image of the pattern has low contrast for that wavelength. Thus, by determining the maximum contrast of the pattern at each part of surface for each wavelength, it is possible to determine the distance of this part of the surface to the objective lens, and thereby determine the object's tomography and topography.

According to another embodiment, the system comprises a broadband and extended light source, an optical element to create a fringe pattern to illuminate the object, an objective lens with chromatic aberration, a spectral imaging optical system to obtain a plurality of images of the object each for a different wavelength. Measurement of the object is obtained by analyzing the resulted images as described above.

In some embodiments, a tunable monochromatic light source is used. A monochrome imager may then be used to obtain images of the object for each of the different tuned wavelengths.

In some embodiments, a spectrally modulated light source is used with a monochrome imager to obtain images of the object for each of the different modulated wavelengths.

In some embodiments the system includes an objective lens with variable focus is used to focus each of the wavelengths at a different image plane. A monochrome imager may be used to obtain multiple images of the object, each for a respective different wavelength.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

In the following description, identical components appearing in more than one figure or sharing similar functionality are referenced by identical reference symbols.

Figure 1:
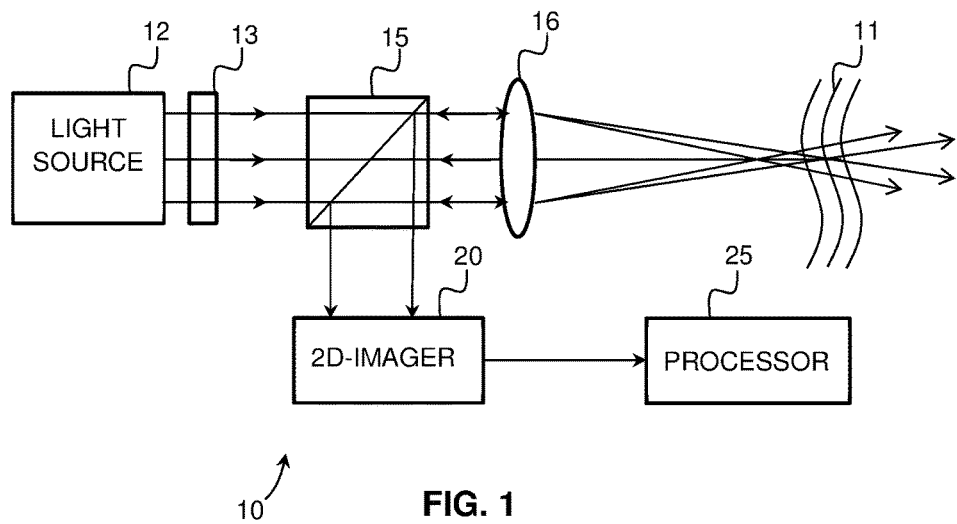
FIG. 1 is a schematic representation of a tomographic and/or topographic measuring system according to a first embodiment.

FIG. 1 is a schematic representation of a full field tomographic and/or topographic measuring system 10 according to a first embodiment for measuring a layered object 11. The system comprises a broadband light source 12, an optical element 13 such as a transparency, a micro lens array or a diffractive optical element in a transmissive or reflective mode that creates a known 2D figure or pattern. In reflective mode, a beam splitter 15 is provided to reflect the light toward the object 11. In transmissive mode, the beam splitter 15 is optional. In some embodiments, an objective lens 16 with chromatic aberration is used to image the known figure or pattern on to the object 11. Due to the chromatic aberration, the objective lens 16 has different wavelength dependent focal lengths. In some other embodiments there is no need for the lens since the optical element 13 itself may have chromatic aberration. When the light propagates through the optical element 13, images of the pattern are created at different planes that are each displaced from the optical element 13 by a different distance that is a known function of the wavelength of the light component striking the object. The patterns do not need to be uniform for all wavelengths. Thus, different patterns or figures may be used to illuminate the object 11 and may be used as a function of the distance from the optical element 13 and/or may also be different for the different wavelengths. A 2D spectral imager 20 acquires the 2D wavelength-dependent images of the figure or pattern on the object 11, and a processing unit 25 coupled to the 2D imager 20 is responsive to the variable image contrast of each image for deriving from the plurality of 2D wavelength dependent patterns an output indicating a tomography and/or topography of the object.

When a certain part of the known pattern or figure of a certain wavelength coincides with part of the object's surface or one of its layer's surfaces, a high contrast 2D image of the known pattern or figure is obtained on that part of the surface. In all other parts of the surface that do not coincide with the image plane, the image of the known pattern or figure for that wavelength is blurred and the contrast of the image is low. Alternatively, when different patterns are employed, a different pattern or figure that is optimized for a different distance may be obtained. The light reflected from the object is gathered and separated into different colors by the spectral imager 20 to obtain the different images of the illuminated object 11 each for a respective wavelength. The respective images for the different wavelengths of the illuminated object are processed and analyzed by the processor unit 25. It is to be noted that, unlike confocal imaging systems of the kind mentioned above, the system 10 according to all embodiments of the invention creates a full 2D image thus avoiding the need for a pinhole or an array of pinholes and thus the need for point-by-point imaging and scanning. Furthermore, in a point by point image the only measurable property of a pixel is its intensity. There is no meaning to the term "contrast" in a confocal single point image that, in effect, has only a single pixel.

The measured displacements from the optical element 13 of the imaged patterns or figures for each wavelength may thus be mapped to respective locations of different points on the object's surface relative to the optical element 13. Since the distances from the optical element 13 of the image planes where the images of the known patterns or figures are known either by design or measurement for all wavelengths, the distances of the different points on the object's surface or its layers surfaces to the optical element 13 can be determined.

In variations of the invention, a tunable monochromatic light source 12 such as a tunable laser may be employed that directs a beam of light through an optical element 13 such as a transparency, a micro lens array or a diffractive optical element in a transmissive or reflective mode to create a known 2D figure or a 2D pattern. In such case, a monochrome 2D imager may be employed. The light source 13 is adjusted to create successive light components of different wavelengths that are thus imaged at different image planes. In other respects the system is as described above.

Figure 2:
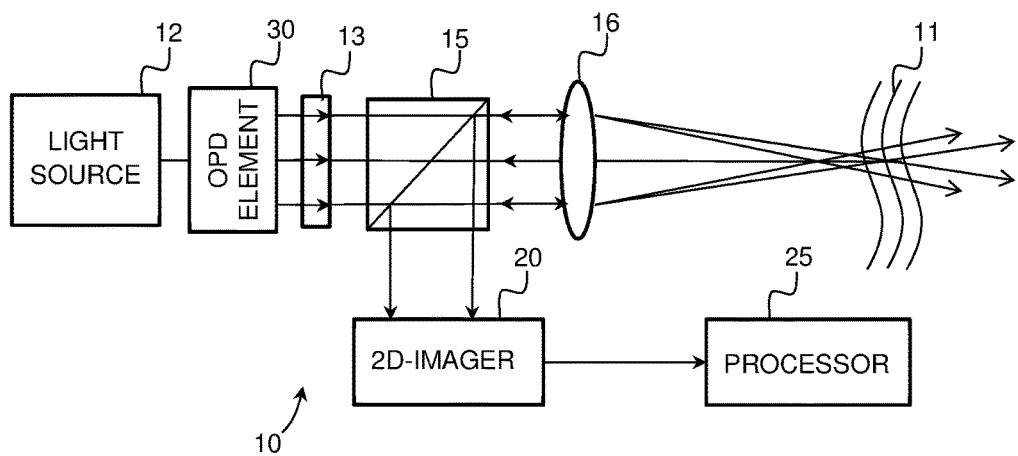
FIG. 2 is a schematic representation of a tomographic and/or topographic measuring system according to a second embodiment.

FIG. 2 shows schematically a system according to another embodiment where an OPD element 30 is disposed between an extended broadband light source 12 and the optical element 13 to create an optical path difference (OPD) between a pair of beams that are divided from the light emanating from the light source 12 and produce interference fringes of the light source 12 at the focal plane of the lens 16. The division may be an amplitude division or a wavefront division. When the divided beams are focused by the lens 16, a fringe pattern is obtained at its focal plane. The interference fringes constitute known patterns are that are produced at the focal plane of the chromatic aberrated lens 16 in which the object 11 is located. Since the lens 16 has chromatic aberration and therefore different focal planes for each wavelength, the fringe patterns of the different wavelengths are created in different focal planes. The form of the pattern and the contrast of the fringes of each wavelength on the object may be used to indicate the depth. The object may be a layered object and each one of the different colors or wavelengths that are focused on the object will be focused in a different axial position and therefore where there is coincidence between an image plane and a reflective surface of the object corresponding to at least part of one its layers should have a maximum contrast of a specific color and/or form at a specific location. By analyzing the images of the illuminated object 11 in different wavelengths, the object's surface or its layers surfaces can be determined as described above.

Figure 3:
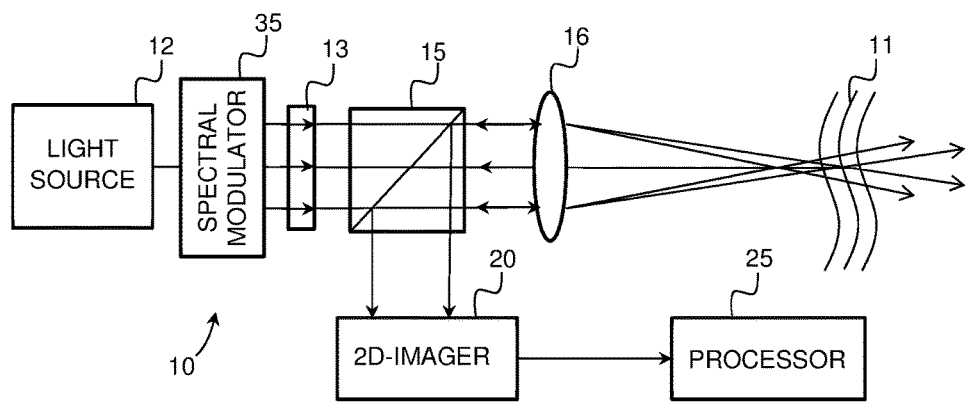
FIG. 3 is a schematic representation of a tomographic and/or topographic measuring system according to a third embodiment.

FIG. 3 shows schematically a system 10 according to another embodiment similar to that shown in FIG. 1 except that a spectral modulator 35 is disposed between the broadband light source 12 and the optical element 13 for modulating the spectrum of the light source 12 with a time varying cosine function. The spectra of the light reflected from each point of the object are calculated by Fourier transformation of the intensity function of time knowing the spectra of the light source. In such an embodiment the 2D imager may be a monochrome device. Once the spectra of the light reflected from each point of the object is known, the 2D images of the illuminated object for each different wavelength can be reconstructed. By combining the distance and the 2D images, 3D tomography and/or topography of the given object surface or layers construction may also be achieved.

Figure 4:
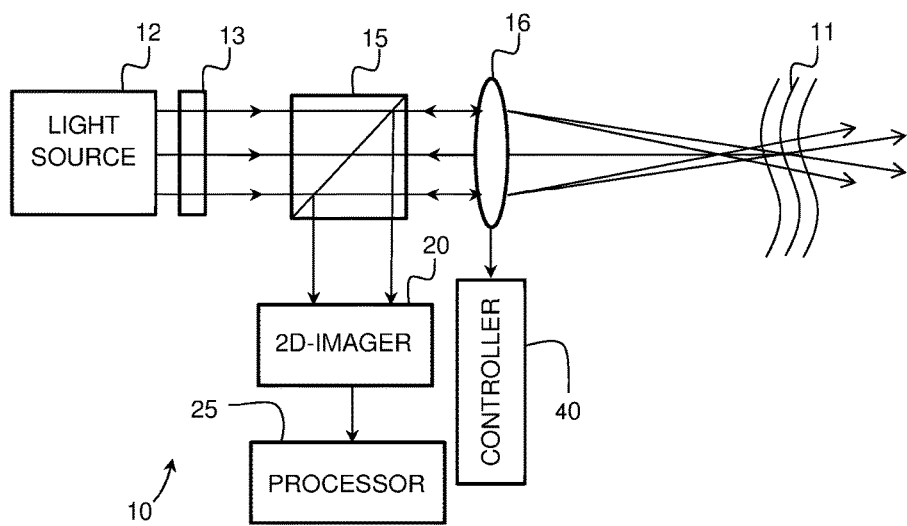
FIG. 4 is a schematic representation of a tomographic and/or topographic measuring system according to a fourth embodiment.

FIG. 4 shows schematically a system 10 according to yet another embodiment similar to that shown in FIG. 1 except that the objective lens 16 has a focal length that may be varied. A controller 40, which may be electronic, mechanical or pneumatic, is operatively coupled to the lens 16 to control and change its focal length. The objective lens 16 may be any kind of optical device or system whose focal length is amenable to variation, such as an LCD lens or a Telephoto optical system. The light source 12 may be either monochromatic or broadband but in the case that it is a broadband light source, the chromatic aberration of the objective lens 16 is corrected for all variable focal lengths so as to have no uncontrolled influence on the focal length of the lens. In this case the 2D imager may be monochrome.

In all of the embodiments, the term "objective lens 16" is also intended to embrace a compound optical system that includes various optical elements such as lens, mirrors, DOEs etc. In addition, the known patterns, images or fringes of the object may also be projected onto the object 11 by an additional optical system (not shown). This allows use of an existing i.e. independent optical system to project the patterns, images or fringes on to the object.

The imaging system that projects and/or images the patterns may be a Scheimpflug system where the optical axis of the objective lens or a component thereof is inclined to an optical axis of at least one other element in the system. The different image planes may also be Talbot image planes when the optical element is periodic and the light source is spatially coherent.

In any of the embodiments described above, the optical element 13 may be a slide that is focused by the objective lens 16 at each component wavelength in different image planes owing to the chromatic aberration of the lens. Alternatively, the optical component may have inherent chromatic aberration such as Diffractive Optical Element (DOE) that causes different patterns to be imaged on different image planes as a function of their respective wavelengths. In this case, the objective lens is not required. The different images of the slide illuminate the object 11. When a certain part of the known pattern or figure of a certain wavelength coincides with part of the object's surface or one of its layer's surfaces, a high contrast image of the slide is obtained on that part of the surface. In all other parts of the surface that do not coincide with the image plane, the image of the slide for that wavelength is blurred and the contrast of the image is low. The light reflected from the object is gathered and dispersed by the spectral imager 20 to obtain the images of the illuminated object 11 in different wavelengths. The different images in different wavelengths of the illuminated object are processed and analyzed by the processor unit 25 as described above.

It will be understood that features that are described with reference to one or more embodiments are described by way of example rather than by way of limitation to those embodiments. Thus, unless stated otherwise or unless particular combinations are clearly inadmissible, optional features that are described with reference to only some embodiments are assumed to be likewise applicable to all other embodiments also.

The invention claimed is:

1. A system for analyzing an object, the system comprising:
   a light source producing multiple light components, each having a respective, different wavelength;
   an optical element configured to direct said light components on to the object and adapted to create known 2D patterns at respective different image planes,
   an image plane of each of the 2D patterns being displaced from the optical element by a distance that is a known function of a wavelength of a respective one of the light components, such that each of the 2D patterns corresponds to light of a given wavelength;
   a 2D imager configured to produce a plurality of images of the 2D patterns,
      each of the images corresponding to a respective 2D pattern, and corresponding to light of a corresponding, respective wavelength, at a corresponding, respective image plane, and
      each of the images having variable image contrast that varies according to displacement of a surface of the object from the respective image plane such that maximal image contrast of the 2D pattern is achieved when the surface of the object and the respective image plane are coincident; and
   a processing unit coupled to the 2D imager and being configured, responsively to the variable image contrast of each of the images, to derive an output indicating a characteristic of the object selected from the group consisting of: a tomography and a topography of the object.

2. The system according to claim 1, wherein the light source comprises a broadband light source.

3. The system according to claim 2, further including an optical path difference element disposed between the broadband light source and the optical element, and configured to create an optical path difference between a pair of beams that are divided from light emanating from the light source and to thereby produce interference fringes from light emanating from the light source.

4. The system according to claim 1, further comprising a spectral modulator configured to spectrally modulate light from the light source.

5. The system according to claim 1, wherein the light source comprises a monochromatic, tunable light source.

6. The system according to claim 1, wherein the imager comprises a 2D monochrome imager.

7. The system according to claim 1, wherein the optical element comprises a slide.

8. The system according to claim 1, wherein the optical element comprises a Diffractive Optical Element.

9. The system according to claim 1, wherein the optical element comprises a micro lens array.

10. The system according to claim 1, wherein the 2D imager comprises a spectral imager.

11. The system according to claim 1, wherein the optical element is configured to create the 2D patterns by generating interference fringes.

12. The system according to claim 1, further comprising an objective lens configured to image the 2D patterns on to the respective image planes.

13. The system according to claim 12, wherein the objective lens has variable focus.

14. The system according to claim 12, wherein the objective lens has chromatic aberrations whereby the 2D patterns are focused on to the respective image planes.

15. The system according to claim 12, wherein an optical axis of the objective lens is inclined with respect to an optical axis of the optical element to thereby constitute a Scheimpflug optical system.

16. The system according to claim 1, wherein the optical element comprises a periodic optical element.

17. The system according to claim 16, wherein the light source comprises a spatially coherent light source, and the optical element is configured to create the known 2D patterns at Talbot image planes.

18. The system according to claim 1, wherein the optical element is adapted to create the known 2D patterns at the respective different image planes, in combination with an objective lens.

19. A method for analyzing an object, the method comprising:
using a light source, producing multiple light components, each having a respective, different respective wavelength;
using at least an optical element, directing the light components on to an object and creating known 2D patterns at respective different image planes,
an image plane of each of the 2D patterns being displaced from the optical element by a distance that is a known function of a wavelength of a respective one of the light components, such that each of the 2D patterns corresponds to light of a given wavelength;
producing a plurality of images of the 2D patterns,
each of the images corresponding to a respective 2D pattern, and corresponding to light of a corresponding, respective wavelength, at a corresponding, respective image plane, and
each of the images having variable image contrast that varies according to displacement of a surface of the object from the respective image plane, such that maximal image contrast of the 2D pattern is achieved when the surface of the object and the respective image plane are coincident; and
using a processing unit, responsively to the variable image contrast of each of the images, deriving an output indicating a characteristic of the object selected from the group consisting of: a tomography of the object and a topography of the object.

* * * * *